United States Patent [19]
Zdrahala et al.

[11] Patent Number: 5,505,887
[45] Date of Patent: Apr. 9, 1996

[54] EXTRUSION PROCESS FOR MANUFACTURING PTFE PRODUCTS

[75] Inventors: Richard J. Zdrahala, Montville; Nicholas Popadiuk, Somerville; Gerald Kalin, Califon; David J. Lentz, Randolph, all of N.J.

[73] Assignee: Meadox Medicals, Inc., Oakland, N.J.

[21] Appl. No.: 209,543

[22] Filed: Mar. 10, 1994

[51] Int. Cl.⁶ ........................... B29C 47/24; B29C 47/86
[52] U.S. Cl. ................. 264/127; 264/209.2; 264/209.8; 264/312; 264/323; 425/144; 425/378.1; 425/381; 425/467
[58] Field of Search ................. 264/209.2, 127, 264/312, 108, 209.7, 209.8, 323; 425/381, 467, 380, 378.1, 144

[56] References Cited

U.S. PATENT DOCUMENTS

| | | | |
|---|---|---|---|
| 2,945,265 | 7/1960 | Sell et al. | 18/59 |
| 3,008,187 | 11/1961 | Slade | 18/14 |
| 3,085,290 | 4/1963 | Chu | 264/127 |
| 3,260,774 | 7/1966 | Harlow | 264/28 |
| 3,382,220 | 5/1968 | Bowman, Jr. | 264/209.7 |
| 3,508,554 | 4/1970 | Sheridan | 264/209.7 |
| 3,907,955 | 9/1975 | Viennot | 264/127 |
| 3,950,118 | 4/1976 | Adair | 425/144 |
| 4,104,394 | 8/1978 | Okita | 264/89 |
| 4,151,242 | 4/1979 | Sansone | 264/209.2 |
| 4,225,547 | 9/1980 | Okita | 264/127 |
| 4,250,138 | 2/1981 | Okita | 264/127 |
| 4,482,516 | 11/1984 | Bowman et al. | 264/127 |
| 4,647,416 | 3/1987 | Seiler, Jr. et al. | 264/127 |
| 4,743,480 | 5/1988 | Campbell et al. | 428/36 |
| 4,876,051 | 10/1989 | Campbell et al. | 264/127 |
| 5,156,785 | 10/1992 | Zdrahala | 264/108 |
| 5,169,587 | 12/1992 | Courval | 264/323 |

FOREIGN PATENT DOCUMENTS

| | | | |
|---|---|---|---|
| 1494939 | 6/1969 | Germany. | |
| 52-72765 | 6/1977 | Japan | 264/127 |
| 56-151535 | 11/1981 | Japan | 264/323 |
| 61-143112 | 6/1986 | Japan | 264/323 |

OTHER PUBLICATIONS

Adhesion and Growth of Cultures Human Endothelial Cells on Perfluorosulphinate: Role of Vitronectin and Fibronectin in Cell Attachment, 1991, Biomaterials, vol. 12, Aug., pp. 531–539.

*Primary Examiner*—Jeffery R. Thurlow
*Attorney, Agent, or Firm*—Hoffmann & Baron

[57] ABSTRACT

An improved extrusion method is employed in a process which is used to form tubing for medical applications. The method includes providing an extrusion apparatus having a die which includes a die cavity and a mandrel within the die cavity. The die is rotated in a first rotational direction while the mandrel is rotated in a second rotational direction opposite the first direction. While the die and the mandrel are rotating, a PTFE paste is passed through the annular passage defined between the die and the mandrel. The die cavity is cooled to maintain the PTFE paste passing therethrough at a substantially non-elevated temperature.

24 Claims, 3 Drawing Sheets

EXTRUSION PROCESS FOR MANUFACTURING PTFE PRODUCTS

FIELD OF THE INVENTION

The present invention relates generally to an extrusion process for use in manufacturing PTFE products. More particularly the present invention relates to an extrusion process for manufacturing PTFE products such as grafts, patches, tubing and the like useful in medical applications.

BACKGROUND OF THE INVENTION

The use of products formed of polytetrafluoroethylene (PTFE) in medical applications is well known. Products such as implantable grafts, implantable patches, catheter tubing and the like may be derived from extruded tubing of PTFE.

PTFE tubing is normally manufactured by a paste extrusion process. Screw injection extrusion which is typical of most thermoplastics may not be effectively used with PTFE because PTFE resin does not exhibit sufficient fluidity even when heated. In the paste extrusion process a "green tube" is formed. A green tube is a tube of PTFE that must be subjected to secondary operations before it yields a usable medical product. Such secondary operations may include stretching and expanding the tube under various conditions of time, pressure and temperature. The paste extrusion process tends to produce a tube which has a fibrous state where its fibrils are generally longitudinally aligned in the direction of extrusion. This fibrous state formation is particularly evident where the PTFE paste includes a lubricant to assist in extrusion. Extruded tubes having fibrils longitudinally aligned in this fashion exhibit low radial or hoop strength. Such a tube is highly susceptible to tearing or rupturing.

Attempts have been made to modify the structure of extruded PTFE tubing. Such attempts seek to manufacture extruded PTFE tubing having non-longitudinally aligned fibrils where the fibrous state formation includes fibrils aligned transversely to the extrusion direction. One attempt in the vascular graft art is shown in U.S. Pat. No. 4,743,480. This technique employs a screw tip on the extrusion mold to reorient the fibrils during the paste extrusion process. The pitch of the screw tip tends to twist the fibrils during extrusion.

In the mechanical art area, U.S. Pat. No. 4,225,547 employs co-rotation to manufacture pipes and wire jackets. In this co-rotation example, the mandrel and the outer portion of the extrusion die are counter-rotated with respect to one another. While this tends to orient the fibrils in both the longitudinal and transverse direction, as set forth in the '547 patent a suitable product is only obtained by heating the tube during extrusion. In this process the die is heated to a temperature significantly above the normal paste temperature. Heating the die while counter rotating the die components results in a product where the fibrous-state formation in the direction perpendicular to extrusion is greatly enhanced.

However, the process described in the '547 patent has several disadvantages. First, heating the metal die components so as to maintain the PTFE paste at an elevated temperature results in thermal expansion of the die components. The differing rates of thermal expansion of these discrete die components may result in gaps being formed between such components. Tubular products formed thereby may exhibit deleterious marks or scarring. Further, leaking of PTFE paste into the die apparatus through the gaps formed between components may adversely effect the operation of the components. Second, lubricant which is normally mixed in with the PTFE paste, to increase fluidity and ease of manufacture, has a tendency to evaporate at elevated temperatures resulting in tubing that is harder and more difficult to handle.

It is therefore desirable to provide a paste extrusion process which overcomes many of the above-evidenced disadvantages.

SUMMARY OF THE INVENTION

It is an object of the present invention to provide an improved extrusion process used in the manufacture of PTFE products.

It is a further object of the present invention to provide an extrusion process for manufacturing PTFE tubing for subsequent use in medical applications.

It is a still further object of the present invention to provide a process for the paste extrusion of PTFE tubing.

In the efficient attainment of these and other objects the present invention provides for the method of forming a PTFE tube. The method includes the steps of providing an extrusion apparatus having an elongate die including a die cavity and an elongate cylindrical mandrel concentrically located within the die cavity. The die and the mandrel are counter-rotated while a PTFE paste is passed through the annular passage defined between the die and the mandrel. The temperature of the die cavity is controlled during extrusion to maintain the PTFE paste passing therethrough at substantially a non-elevated temperature.

As more particularly described by way of the preferred embodiment shown herein, the present invention provides for the rotation of a portion of the die in a first rotation direction and the rotation of the mandrel in a second rotation direction opposite the first rotation direction. Further, the relative speeds of rotation of the die and the mandrel are varied so that one of the die or mandrel is rotating faster than the other. In addition, the control of the temperature of the die is achieved by interposing a cooling substance around the die to cool the PTFE paste being extruded therethrough.

DETAILED DESCRIPTION OF THE PREFERRED EMBODIMENT

Figure 1:
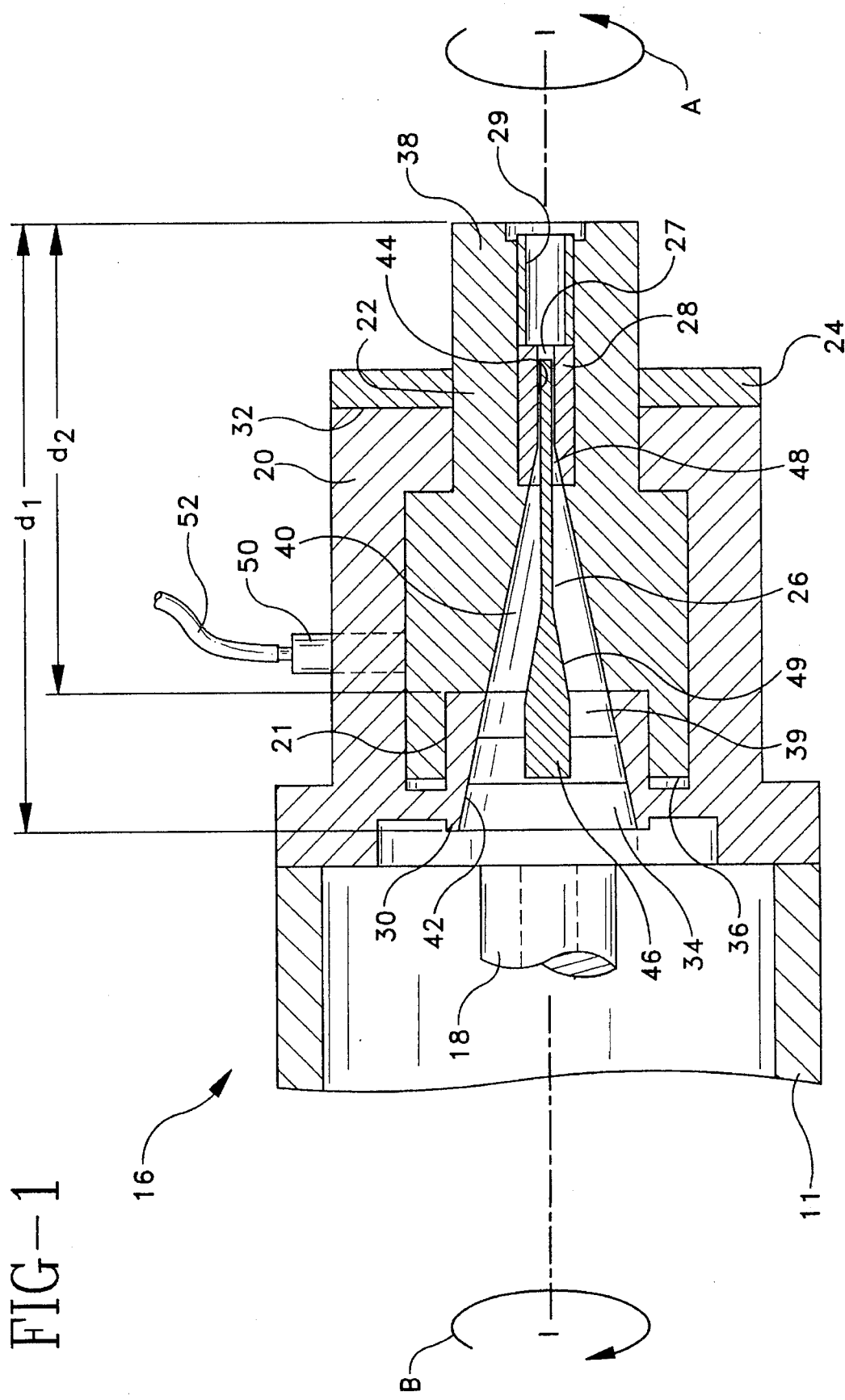
FIG. 1 shows in schematic section the die apparatus used to extrude a PTFE tube.

An extrusion apparatus 10 used to form an extruded PTFE tube 12 (FIG. 3) is shown with reference to FIG. 1. The extrusion apparatus 10 includes a conventional extruder 11 which accepts PTFE paste. As stated above, the process of the present invention employs a paste extrusion process where PTFE resin is mixed with liquid lubricant. As is well known in the PTFE extrusion art, a lubricant is used to render the PTFE paste more fluid and easier to extrude and handle after it is formed into a tube. A PTFE paste of resin and lubricant is formed in a preform press (not shown) into a preform product referred to as a tubular billet 18. Tubular billet 18 is loaded into the extruder 11 in a position where it may be fed into a die apparatus 16 in a manner which is also well known in the extrusion art.

In the present invention die apparatus 16 is a multi-component device including a stationary die body 20, a rotating die element 22, a supporting plate 24 which supports die element 22 to die body 20, a mandrel 26, a die insert 28 and an insert spacer 29. Each of the die apparatus components are typically formed of metal, preferably stainless steel.

Die body 20 is generally an elongate hollow cylindrical member having a first end 30 for receiving billet 18, a second end 32 for rotationally supporting die element 22 and a central bore 34 therethrough. Die body 20 is supported by the extruder 11 in a fixed non-movable position with respect thereto.

Die element 22 is generally an elongate hollow cylindrical member having a first end 36 which is supported adjacent first end 30 of die body 20. Die element 22 also includes an opposed second end 38 which extends outwardly beyond second end 32 of die body 20. A central bore 39 is defined between the first end 36 and the second end 38 of die element 22. Bore 39 of die element 22 is in communication with bore 34 of die body 20 and together with mandrel 26 define a generally narrowing annular extrusion bore 40 for passage of tubular billet 18 in a manner which will be described in further detail hereinbelow.

Supporting plate 24 secures die element 22 to die body 20. Various fastening techniques may be used to support supporting plate 24 to die body 20 to secure die element 22 thereto.

Die apparatus 16 further includes an elongate hollow generally cylindrical die insert 28 positioned within bore 39 of die element 22 adjacent second end 38 thereof. Die insert 28 has a central bore 27 therethrough. As will be described in further detail hereinbelow, die insert 28 is used to form and regulate the outside dimension (O.D.) of tube 12 which is extruded through die apparatus 16. Die insert 28 may be interchanged with differently sized die inserts to vary the O.D. of tube 12 formed thereby.

A die spacer 29 is used to support and position die insert 28 within bore 39 of die element 22.

Bore 34 of die body 20, bore 39 of die element 22 as well as bore 27 of die insert 28 are each longitudinally aligned in successive communicative position, and together with mandrel 26 form a die cavity coextensive with elongate extrusion bore 40 for the passage of tubular billet 18. Extrusion bore 40 is generally conical in shape having a wider end 42 for receiving billet 18 and a narrow cylindrical end 44 for the formation of tube 12.

Mandrel 26 of die apparatus 16 is an elongate generally cylindrical member centrally positioned within bore 40. A cylindrical end 46 of mandrel 26, adjacent first end 30 of die body 20, is wider than the opposite cylindrical end 48 adjacent die insert 28. A central conically tapered section 49 of mandrel 26 provides a transition between wider end 46 and narrower opposite end 48. Cylindrical end 48 of mandrel 26 is positioned centrally within bore 27 of die insert 28 and forms the inner diameter (I.D.) of tube 12.

As described above, die element 22 is supported within die body 20 for relative rotational movement with respect thereto. As die element 22 is constructed to rotate with respect to die body 20, a resilient sealing member (not shown) may be interposed between the interface 21 of the two components to form a seal thereat.

A conventional mechanism (not shown) may be secured to die element 22 to effect rotational movement thereof. Further, a conventional mechanism (also not shown) may be secured to mandrel 26 to effect its rotational movement. Die element 22 and mandrel 26 are designed to be rotated in opposite relative rotational directions. As shown in FIG. 1, die element 22 may be rotated in the rotational direction of arrow A, while mandrel 26 may be rotated in the rotational direction of arrow B, which is opposite of arrow A. As will be described in further detail hereinbelow, the conventional mechanisms used to rotate die element 22 and mandrel 26 may also vary the rotational speeds of each of die element 22 and mandrel 26.

The present invention further contemplates varying the length of the rotating outer portion of die apparatus 16, by varying the length of rotating die element 22. As shown in FIG. 1, bore 40 defined between first end 30 of die body 20 and the second end 38 of die element 22 along center line l, has an overall length of $d_1$. A lesser portion $d_2$ of this length, defined solely by rotating die element 22, is rotatable. In the present illustrative example $d_2$ may be between about 50% and 100% of $d_1$, preferably $d_2$ may be between about 70% and 100% of $d_1$. It has been found that results such as those described hereinbelow may be varied by varying the length of the rotating portion of die apparatus 16.

Additionally, die body 20 further includes cooling connection ports 50 thereon. Connection ports 50 connect fluid tubes 52 to die body 20. This permits a chilled liquid coolant to be circulated around die body 20 so as to cool the die apparatus 16 during the extrusion process. The counter-rotative movement of mandrel 26 and die element 22 generates frictional heat which would be imparted to the tube 12 extruded therebetween. By circulating a cooling medium throughout die apparatus 16, significant heat rise is prevented.

Having described the structure of die apparatus 16, its operation may now be described.

Preformed tubular billet 18 is loaded into the extruder 11. Mandrel 26 is caused to rotate in the direction of arrow B and die element 22 is caused to rotate in the direction of arrow A. While providing such simultaneous counter-rotation of mandrel 26 and die element 22, tubular billet 18 is extruded through the bore 40. The extruded PTFE paste passes through die insert 28 to take the tubular shape shown in FIG. 3. The exiting tubular extrusion may be cut to any desired length.

As described above, conventional extrusion processes have a tendency to align the fibrils of extruded product along the direction of extrusion. Fibrils aligned in this manner result in a tube having low radial strength. By counter-rotating the mandrel and the die, a structure of tube 12 is formed having non-aligned fibrils (FIG. 3) which increase the radial tear strength of the tube. The rotation of die element 22 imparts a helical fibril pattern to the outside of tube 12. Similarly the rotation of mandrel 26 in a direction opposite that of die element 22 imparts a helical fibril pattern to the inside of tube 12 which is opposite the helical pattern of the outside of the tube.

However, in the prior art practices of counter-rotating die components, the desired non-aligned fibril structure is formed in a heated environment. Such heating could be externally induced or could be caused by the normal friction between the rotating parts. The present invention provides an extruded tube 12 having a desired non-aligned fibril structure without subjecting the die components to elevated temperatures. While the PTFE paste is being extruded through the die apparatus 16, it is prevented from heating to an elevated temperature. The friction caused by the relatively rotating parts could cause the die apparatus 16 to have a temperature rise well in excess of 125° F. By passing a cooling fluid through tube 52 and ports 50 during extrusion, the die apparatus 16 may be controlled and maintained at a substantially non-elevated temperature. In fact, it has been found that superior results are achieved by cooling the die apparatus 16 to between ambient temperature and about 100° F., preferably between about 60° F. and about 90° F. and specifically about 75° F. Maintaining die apparatus 16 at a non-elevated temperature provides two distinct advantages. First, it prevents gaps between die components resulting from thermal expansion of the die components. Second, it prevents evaporation of the lubricant in the PTFE paste during extrusion.

Figure 3:
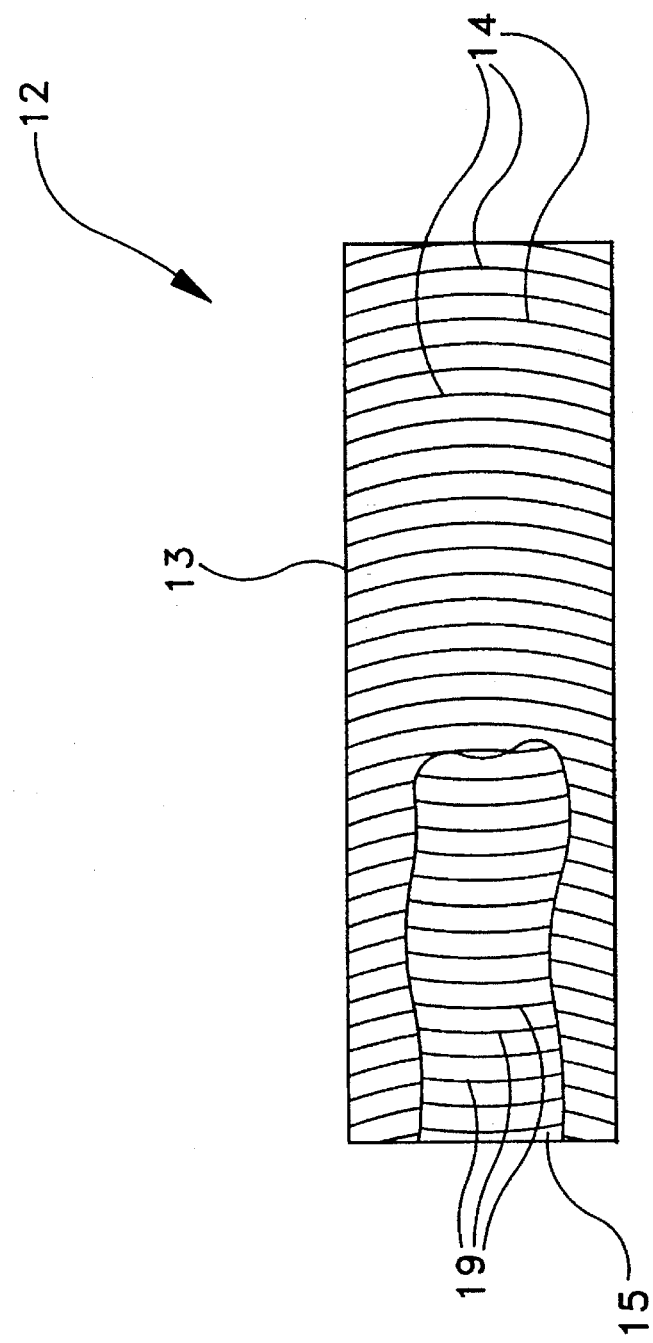
FIG. 3 is a perspective view partially broken away, of a PTFE tube formed in accordance with the present invention, showing schematically the fibrous state formation of the extruded tube.

Referring to FIG. 3, the fibrous structure of the tube 12 of the present invention is schematically represented. Tube 12 formed in accordance with the present invention shows the results of counter rotating die element 22 with respect to mandrel 26 during extrusion. The outer surface 13 of tube 12 has fibril orientation 14 generally in a helical pattern. The direction of the helical fibril orientation 14 corresponds to the rotation direction A of die element 22 resulting from the outer surface 13 of tube 12 being in contact with rotating second die element 22 during extrusion. Similarly, the inner surface 15 of tube 12 has a fibril orientation 19 in a helical pattern which is opposite that of fibril orientation 14 on the outer surface 13 of tube 12. The helical pattern on inner surface 15 corresponds to rotation direction B of mandrel 26 resulting from the inner surface 15 of tube 12 being in contact with rotating mandrel 26 during extrusion. As rotation direction A is opposite that of rotation direction B, the helical fibril orientation 14 and 19 are also opposite one another. With respect to both outer surface 13 as well as inner surface 15 of tube 12, the effect of counter-rotation on the fibril orientation can be seen. Significant fibril orientation in a non-longitudinally aligned direction is achieved.

It is further contemplated that different degrees of helical fibrous structure may be achieved by varying the relative rotational rates of mandrel 26 and die element 22 (FIG. 1). Also, as above mentioned, the helical fibrous structure may also be changed by varying the length of the rotating die element 22 with respect to stationary die body 20. Generally, as the length of the rotating component is increased or as the relative rotation rates of the counter rotating parts is increased, an increase in the fibrous formation in a non-longitudinally aligned direction may be observed with an associated increase in radial tear strength.

Table I summarizes the resulting radial tear strength imparted to a tube formed in accordance with the FIG. 1 embodiment of the present invention, where the relative rates of rotation of mandrel 26 and die element 22 are varied.

TABLE I

| # | Die RPM | Mandrel RPM | Radial Strength (kg) |
|---|---|---|---|
| Sample 1 (Control) | No Rotation | No Rotation | 0.484 |
| Sample 2 | 72 | 125 | 1.520 |
| Sample 3 | 104 | 125 | 1.050 |
| Sample 4 | 104 | 250 | 1.260 |
| Sample 5 | 153 | 260 | 1.700 |
| Sample 6 | No Rotation | 30 | 0.600 |

As can be seen, differences between the relative rates of rotation of the die element 22 and the mandrel 26 result in various increases in radial strength of the resulting product over the control sample extruded without rotation of either die component. Even rotation of only one of die element 22 or mandrel 26, as in sample 5 where only mandrel 26 is rotated, results in superior radial strength. Generally it can be seen that by varying the relative rotational rates of mandrel 26 and die element 22, the non-alignment of fibrils of tube 12 will be enhanced so as to increase the radial strength of tube 12 over that formed without counter-rotation.

Figure 2:
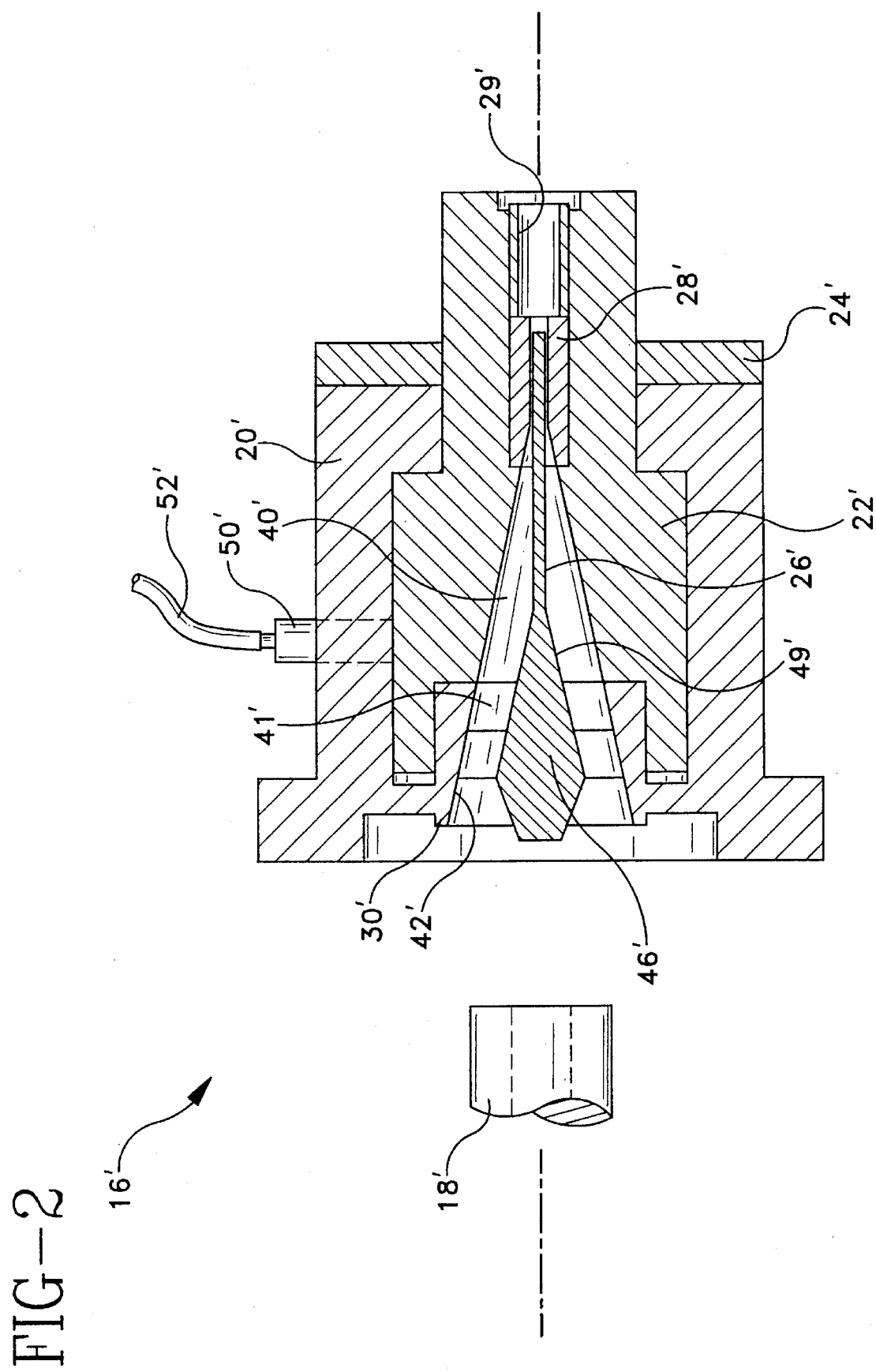
FIG. 2 shows in schematic section, a further embodiment of a die apparatus used to extrude a PTFE tube.

Referring now to FIG. 2, a further embodiment of the present invention is shown. Die apparatus 16' is substantially similar to die apparatus 16 shown in FIG. 1 (like reference numerals referring to like components). In the die apparatus 16' shown in FIG. 2, mandrel 26' is modified from that shown in FIG. 1. One end 46' of mandrel 26 is formed to have an overall conical configuration along a longitudinal extent 41'. End 46' is positioned such that extent 41' is aligned with a central portion of bore 40'. The conical configuration of extent 41' matches the conical configuration of bore 40' adjacent thereto. As wider end 46' now tapers to match the taper of bore 40' thereat, a generally uniformly tapering annular cavity extent is formed therebetween. This is in distinction to the embodiment shown in FIG. 1 where the wider end 46 of mandrel 26 is generally cylindrical while the bore 40 thereadjacent is tapered or conical.

In the embodiment shown in FIG. 2, it is contemplated that the extrusion of tubular billet 18' may be more easily facilitated through an annular bore which generally is of uniform bore width over a longitudinal extent. This reduces the tendency to force billet 18' into a chamber which abruptly narrows. The billet 18' is more easily passed through bore 40' with less resistance being encountered as the paste passes towards extrusion die 28'. This resulting ease of passage allows the mandrel 26' and die element 22' to be rotated at slower rates of rotation, i.e. slower RPM's, and still provide a suitable helical formation of the fibers during extrusion. The slower rates of rotation of mandrel 26' and die element 22' assists in preventing excessive heat build-up of die apparatus 16' which as described above, is advantageous in providing a tube 12 which is more pliable and easier to handle.

Table II summarizes the resulting radial strength imparted to a tube formed in accordance with the FIG. 2 embodiment of the present invention.

TABLE II

| # | Die RPM | Mandrel RPM | Radial Strength (kg) |
|---|---|---|---|
| Sample 1 | 10 | 20 | 0.676 |
| Sample 2 | 60 | 80 | 1.277 |
| Sample 3 | 60 | 120 | 0.778 |
| Sample 4 | 125 | 250 | 0.889 |
| Sample 5 | No Rotation | 30 | 0.640 |

As can be seen by a comparison of Table I with Table II, tubes with significantly increased radial strength (over the control sample, Table I) can be formed with relatively low rates of rotation of mandrel 26' and die element 22'. By reducing the relative rates of rotation of the mandrel and die element while still producing a tube with high radial strength, the overall efficiency and ease of operation of the process described herein may be achieved.

Various changes to the foregoing described and shown structures would now be evident to those skilled in the art.

Accordingly the particularly disclosed scope of the invention is set forth in the following claims.

What is claimed is:

1. A method of forming a tubing material, comprising the steps of:

providing an extrusion apparatus having an elongate die defining a die cavity and an elongate mandrel substantially concentrically located within said die cavity;

rotating a portion of said die in a first rotation direction;

rotating said mandrel in a second rotation direction opposite said first direction;

passing a PTFE paste through an elongate passage defined between said rotating die and said rotating mandrel;

cooling said die cavity to maintain said PTFE paste passing through said passage at a substantially non-elevated temperature; and extruding said PTFE paste through an extrusion die located at one end of said elongate passage whereby helical fibrous formation of said tubing material is enhanced.

2. A method in accordance with claim 1 wherein said die has a first elongate die portion and a second elongate die portion, said second elongate die portion being adjacent said extrusion die and wherein said first and second die portions define a conically shaped die cavity tapering toward said extrusion die.

3. A method in accordance with claim 2 wherein said die rotating step includes rotating said second die portion.

4. A method in accordance with claim 3 wherein said elongate first and second die portions are of unequal lengths.

5. A method in accordance with claim 3 wherein the ratio of the length of said second die portion to the length of said first die portion ranges from about 1:1 to about 9:1.

6. A method in accordance with claim 5 wherein the ratio of the length of said second die portion to the length of said first die portion ranges from about 7:3 to 9:1.

7. A method in accordance with claim 1 wherein said die rotating step includes rotating said portion of said die at a first rotational speed, and wherein said mandrel rotating step includes rotating said mandrel at a second rotational speed different from said first rotating speed.

8. A method in accordance with claim 7 wherein said second rotational speed is greater than said first rotational speed.

9. A method in accordance with claim 1 wherein said cooling step includes passing a chilled liquid around said die.

10. A method in accordance with claim 9 wherein said cooling step further includes maintaining said PTFE paste at a temperature from about 60° F. to about 100° F.

11. A method of forming an elongate extruded tube comprising the steps of:

forming a PTFE preform product;

providing an extrusion apparatus including an elongate die having an internal die cavity and an elongate mandrel within said die cavity to thereby define a generally tubular die chamber therebetween;

placing said preform product in said extrusion apparatus;

rotating at least a portion of said die in a first direction;

rotating at least a portion of said mandrel in a second direction opposite said first direction;

extruding said preform product through said die chamber between said oppositely rotating die and mandrel portions to form said tube; and cooling said preform product during said extruding step whereby said formed extruded tube exhibits substantial fibrous formation in a direction non-longitudinally aligned with said tube.

12. A method in accordance with claim 11 wherein said extrusion apparatus further includes a die insert at one end of said die chamber and wherein said extruding step further includes extruding said preform product through said die insert to form said tube.

13. A method in accordance with claim 12 wherein said die further includes a first die portion and a second die portion, said second die portion located adjacent said die insert and wherein said die rotating step includes rotating said second die portion.

14. A method in accordance with claim 12 wherein said cooling step includes interposing a cooling substance around said die.

15. A method in accordance with claim 13 wherein said mandrel is rotated at a first speed and said second die portion is rotated at a second speed different from said first speed.

16. A method of forming a PTFE tube comprising the steps of:

providing an extrusion apparatus having an elongate die defining a die cavity and an elongate mandrel substantially concentrically located within said die cavity, rotating one of said die or said mandrel;

passing a PTFE paste through an elongate annular passage defined between said die and said mandrel;

controlling the temperature of said die cavity to maintain said PTFE paste passing through said annular cavity at a substantially non-elevated temperature; and extruding said PTFE paste through an extrusion die located at one end of said elongate passage whereby fibrous state formation of said formed tube is enhanced in a direction which is non-aligned with said elongate annular passage.

17. A method of claim 16 wherein said rotating step includes:

rotating said tubular die in a first direction; and rotating said mandrel in a second direction opposite said first direction.

18. A method of claim 17 wherein said tubular die includes a first die portion and a second die portion, said second die portion being adjacent said extrusion die and whereby said tubular die rotation step includes rotating said second die portion in said first direction and maintaining said first die portion stationary.

19. A method of claim 16 wherein said controlling step includes cooling said die cavity.

20. A die apparatus for extruding PTFE tubes comprising:

a die body having a passage for receipt of a PTFE preform;

a die element having an elongate central bore therethrough in communication with said passage of said die body;

a tubular extrusion die supported at one end of said central bore of said die element and forming therewith an elongate die cavity for extrusion therethrough of said preform;

an elongate mandrel positioned within said die cavity, said mandrel being rotatably supported within said die cavity for rotation in a first rotational direction;

means for rotating said mandrel in said first rotational direction; and temperature control means coupled to said die body for maintaining said die cavity adjacent said rotating mandrel at a substantially non-elevated temperature.

21. A die apparatus of claim 20 wherein said die element is rotatably positioned with respect to said die body for rotation in a second rotational direction opposite said first rotational direction.

22. A die apparatus of claim 21 wherein said temperature control means includes cooling means for cooling said die cavity.

23. A die apparatus of claim 22 wherein said cooling means includes said die body having a coolant entry port coupled thereto for receiving a liquid coolant for dispersement around said die element for retarding heat rise occasioned by the rotation of said die element.

24. A die apparatus of claim 23 wherein said die cavity is maintained at a temperature not substantially exceeding 75° F.

* * * * *

UNITED STATES PATENT AND TRADEMARK OFFICE
CERTIFICATE OF CORRECTION

PATENT NO. : 5,505,887
DATED : April 9, 1996
INVENTOR(S) : Zdrahala et al.

It is certified that error appears in the above-indentified patent and that said Letters Patent is hereby corrected as shown below:

At column 2, line 58 "used to forman" should read --used to form an--.

Signed and Sealed this

Thirtieth Day of July, 1996

Attest:

BRUCE LEHMAN

Attesting Officer

Commissioner of Patents and Trademarks